US012797260B2

(12) United States Patent
Sharma et al.

(10) Patent No.: US 12,797,260 B2
(45) Date of Patent: Nov. 17, 2026

(54) MEDICAL SYSTEMS, DEVICES, AND RELATED METHODS

(71) Applicant: Boston Scientific Medical Device Limited, Galway (IE)

(72) Inventors: Deepak Kumar Sharma, Muzaffarnagar (IN); Sharath Kumar G, Kanakapura (IN); Rajivkumar Singh, Thane (IN)

(73) Assignee: Boston Scientific Medical Device Limited, Galway (IE)

( * ) Notice: Subject to any disclaimer, the term of this patent is extended or adjusted under 35 U.S.C. 154(b) by 332 days.

(21) Appl. No.: 18/483,683

(22) Filed: Oct. 10, 2023

(65) Prior Publication Data

US 2024/0122769 A1 Apr. 18, 2024

Related U.S. Application Data

(60) Provisional application No. 63/379,324, filed on Oct. 13, 2022.

(51) Int. Cl.
*A61F 13/26* (2006.01)
*A61B 1/00* (2006.01)
(Continued)

(52) U.S. Cl.
CPC ........ *A61F 13/266* (2013.01); *A61B 1/00087* (2013.01); *A61F 13/2074* (2013.01); *A61F 2013/2014* (2013.01)

(58) Field of Classification Search
CPC ................ A61F 13/266; A61F 13/2074; A61F 2013/2014; A61F 2/0063; A61F 2/04; A61F 2002/0072; A61F 2002/045; A61B 1/00087; A61B 2017/00296; A61B 2017/00367; A61B 2017/0061; A61B 2017/00623; A61B 2017/00632; A61B 2017/00818; A61B 2017/00867;
(Continued)

(56) References Cited

U.S. PATENT DOCUMENTS 4,326,530 A * 4/1982 Fleury, Jr. .............. A61B 18/14 606/47
6,007,551 A * 12/1999 Peifer .............. A61B 17/12013 606/139
(Continued)

FOREIGN PATENT DOCUMENTS

DE 212018000416 U1 3/2021

*Primary Examiner* — Tan-Uyen T Ho
*Assistant Examiner* — Osama Nemer
(74) *Attorney, Agent, or Firm* — Bookoff McAndrews PLLC

(57) ABSTRACT

A medical device includes a handle, an end cap, and a patch. The handle includes a movable body and a stationary body. The movable body includes an actuation member. The end cap is configured to be coupled to a distal end of a scope. The patch is movable relative to the end cap. The patch is coupled to the movable body via one or more control elements such that movement of the movable body extends the patch from the end cap. The patch is further coupled to the actuation member via one or more actuation elements such that movement of the actuation member extends, bows, or bends the one or more actuation elements to at least partially deploy the patch.

20 Claims, 7 Drawing Sheets

(51) Int. Cl.
*A61B 17/00* (2006.01)
*A61F 13/20* (2006.01)

(58) Field of Classification Search
CPC A61B 2017/00884; A61B 2017/00893; A61B 2017/00907; A61B 2017/00951; A61B 2017/12004; A61B 17/0057; A61B 1/00131; A61B 1/00137; A61B 1/0014; A61B 2017/00575; A61B 2017/00597; A61B 17/00234; A61B 17/3468; A61L 24/00
See application file for complete search history.

(56) References Cited

U.S. PATENT DOCUMENTS

| | | | | |
|---|---|---|---|---|
| 7,530,983 | B1 * | 5/2009 | Jenkins | A61B 17/32056 606/110 |
| 7,547,310 | B2 * | 6/2009 | Whitfield | A61B 17/221 606/114 |
| 7,691,110 | B2 * | 4/2010 | Secrest | A61B 17/3478 606/113 |
| 8,142,347 | B2 * | 3/2012 | Griego | A61B 17/32056 600/113 |
| 9,113,848 | B2 * | 8/2015 | Fleming | A61B 17/00234 |
| 11,554,251 | B2 * | 1/2023 | King | A61M 25/0074 |
| 2005/0131279 | A1 * | 6/2005 | Boulais | A61B 1/0016 600/141 |
| 2020/0038005 | A1 * | 2/2020 | Smith | A61L 24/08 |
| 2020/0046343 | A1 * | 2/2020 | Kramer | A61B 17/0482 |
| 2021/0059677 | A1 * | 3/2021 | Jin | A61B 17/122 |

* cited by examiner

MEDICAL SYSTEMS, DEVICES, AND RELATED METHODS

CROSS-REFERENCE TO RELATED APPLICATIONS

This application claims the benefit of priority under 35 U.S.C. § 119 from U.S. Provisional Application No. 63/379, 324, filed Oct. 13, 2022, which is incorporated by reference herein in its entirety.

TECHNICAL FIELD

The disclosure relates generally to systems, devices, and methods for delivering patches. More specifically, aspects of the disclosure pertain to systems, devices, and/or methods for delivering patches, for example, for hemostasis, via medical devices, such as endoscopes.

BACKGROUND

Bleeding ulcers, for example, in a subject's gastrointestinal (GI) tract, are often difficult to manage and/or provide hemostasis. For example, common treatments for bleeding ulcers include injection therapies, thermal therapies, mechanical therapies, and hemostatic powders. Such therapies are often expensive and/or time-consuming. Furthermore, such therapies may not be able to treat a larger surface area, for example, a larger ulcer in the GI tract. Additionally, a common treatment for chronic ulcers is a gastric bypass. Such procedures may be more difficult, more time-consuming, more costly, and/or less effective/accurate than a minimally-invasive procedure to position a patch on one or more ulcers. Therefore, a need exists for systems, devices, and/or methods for positioning and/or deploying one or more hemostatic patches with one or more portions of a subject.

SUMMARY

This disclosure includes medical systems and devices comprising a biocompatible patch and methods of use thereof, e.g., methods of delivering a patch to a target site of a patient, for example, to help heal an ulcer and/or to perform hemostasis.

In one or more examples, a medical device may include a handle, an end cap, and a patch. The handle may include a movable body and a stationary body. The movable body may include an actuation member. The end cap may be configured to be coupled to a distal end of a scope. The patch may be movable relative to the end cap. The patch may be coupled to the movable body via one or more control elements such that movement of the movable body may extend the patch from the end cap. The patch may be further coupled to the actuation member via one or more actuation elements such that movement of the actuation member may extend, bow, or bend the one or more actuation elements to at least partially deploy the patch.

The medical device may include one or more of the following features. The actuation member may be movably positioned within a slot on the movable body of the handle. The end cap may include an outer cap and an inner cap, and the patch may be movably positioned between the outer cap and the inner cap. The inner cap may include a prong extending radially inward and configured to abut a distal end face of the scope. The medical device may further include a protective element positioned at a distal end of the one or more actuation elements and may be configured to at least partially seal an opening between the outer cap and the inner cap.

The patch may include one or more retention grooves configured to receive a portion of the one or more actuation elements to couple the patch to the one or more actuation elements. The one or more retention grooves may be positioned on a radially exterior portion of the patch when the patch is in an undeployed configuration. The end cap may include an end cap ring, and at least a portion of the end cap may be transparent. The one or more actuation elements may be formed of a shape-memory material.

The medical device may further include one or more sheath elements coupling the handle to the end cap. Each of the one or more actuation elements may be movably positioned within one of the one or more control elements. Each of the one or more control elements may be movably positioned within one of the one or more sheath elements. The one or more actuation elements may each be formed of one or more wires, and the one or more control elements may each be formed of one or more coils. The movable body of the handle may be movable within a slot in the stationary body of the handle. The movable body of the handle may include at least one peg. The stationary body of the handle may include at least one hole, and the at least one peg may be configured to engage with the at least one hole to at least partially secure a position of the movable body on the stationary body. The position of the at least one hole on the stationary body may correspond to a position of the movable body on the stationary body in which the patch is extended from the end cap. The patch may include a hemostatic agent.

In another aspect, a medical system may include an endoscope and a medical device. The endoscope may include a distal end including one or more visualization devices on a distal end face. The medical device may include a handle, an end cap, and a patch. The handle may include a movable body and a stationary body. The movable body may include an actuation member. The end cap may be configured to be coupled to a radial exterior of the distal end of the endoscope. The patch may be movable relative to the end cap. The patch may be coupled to the movable body via one or more control elements such that movement of the movable body extends the patch from the end cap. The patch may be further coupled to the actuation member via one or more actuation elements such that movement of the actuation member at least partially deploys the patch.

The medical system may include one or more of the following features. The end cap may include an outer cap and an inner cap. The patch may be movably positioned between the outer cap and the inner cap. The inner cap may include a prong extending radially inward and configured to abut the distal end face of the endoscope. The medical system may further include a protective element positioned at a distal end of the one or more actuation elements and configured to at least partially seal an opening between the outer cap and the inner cap. The patch may include one or more retention grooves configured to receive a portion of the one or more actuation elements to couple the patch to the one or more actuation elements. Movement of the one or more actuation elements may extend, bow, or bend the one or more actuation elements radially outward and out of the one or more retention grooves.

In yet another aspect, a medical device may include a handle, an end cap, and a patch. The handle may include a movable body and a stationary body. The movable body may include an actuation member that is movable within a slot in the movable body. The end cap may be configured to be coupled to a distal end of a second medical device. The end cap may include an outer cap and an inner cap. The patch may be movably positioned between the outer cap and the inner cap. The patch may be coupled to the movable body via one or more control elements such that distal movement of the movable body extends the patch from the end cap. The patch may further be coupled to the actuation member via one or more actuation elements such that movement of the actuation member at least partially deploys the patch.

The inner cap may include a prong that may extend radially inward and may be configured to abut a distal end face of the second medical device. The patch may include one or more retention grooves, which may be configured to receive a portion of the one or more actuation elements to couple the patch to the one or more actuation elements. Movement of the one or more actuation elements may cause the one or more actuation elements to extend, bow, or bend radially outward and out of the one or more retention grooves, which may at least partially deploy the patch.

Any of the examples described herein may have any of these features in any combination.

It may be understood that both the foregoing general description and the following detailed description are exemplary and explanatory only and are not restrictive of the invention, as claimed. As used herein, the terms "comprises," "comprising," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate examples of this disclosure and together with the description, serve to explain the principles of the disclosure.

DETAILED DESCRIPTION

Reference is now made in detail to examples of this disclosure, aspects of which are illustrated in the accompanying drawings. Wherever possible, the same reference numbers will be used throughout the drawings to refer to the same or like parts.

Figure 1:
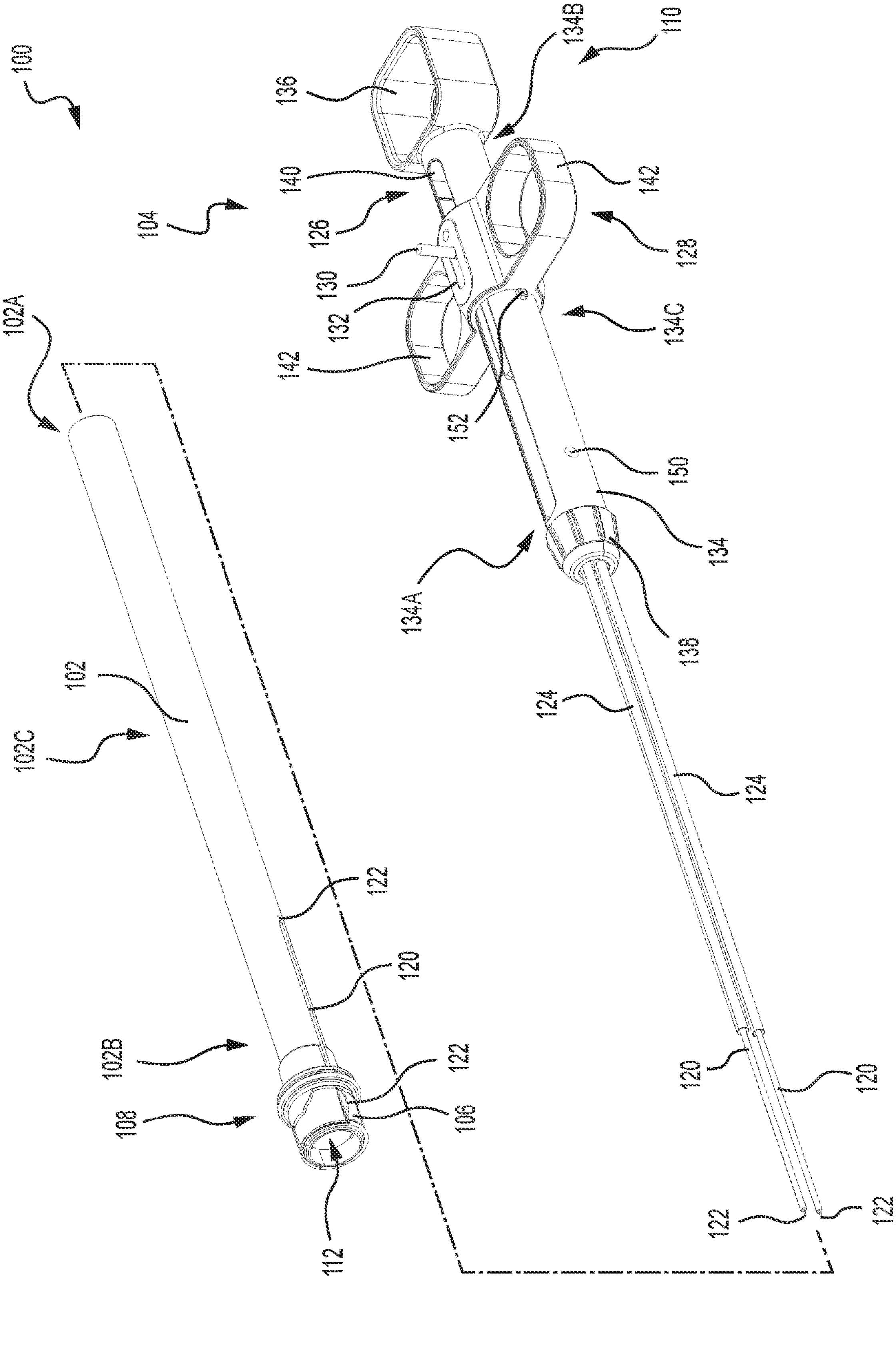
FIG. 1 depicts a perspective view of an exemplary medical system, including an exemplary medical device and an endoscope.

FIG. 1 illustrates a medical system 100, for example, including an endoscope 102 and a medical device 104. As discussed in detail herein, medical device 104 may include or otherwise be coupled to a patch delivery system, for example, to position and/or deliver a patch 106 to one or more portions of tissue within a subject, which may help perform hemostasis within the subject. Moreover, medical device 104 may be coupled to one or more portions of endoscope 102, for example, in order to deliver one or more portions of medical device 104 to a treatment site. For example, medical device 104 may include an end cap 108. End cap 108 may be coupled a distal portion 102B (i.e., a distal end) of endoscope 102, such that end cap 108 and distal portion 102B of endoscope 102 may be delivered to the treatment site. Additionally, patch 106 may be positioned within or internal to one or more portions of end cap 108 during the delivery. A portion of end cap 108 is omitted in FIG. 1 to expose patch 106 and other aspects of medical device 104. Medical device 104 may include a handle 110, and manipulation of one or more portions of handle 110 may help to maneuver, position and/or reposition, release or deploy, and/or deliver patch 106, for example, to position patch 106 over tissue at the treatment site.

Endoscope 102 may include a generally cylindrical tubular shape, and may include a proximal portion 102A, distal portion 102B, and an intermediate portion 102C. Although not shown, proximal portion 102A may include or otherwise be coupled to a handle, for example, including one or more ports, controls, levers, electrical or communication connections, etc. Additionally, endoscope 102 may include one or more internal lumens 112 or working channels, for example, extending longitudinally through endoscope 102. In these aspects, internal lumens 112 or working channels may extend through proximal portion 102A, intermediate portion 102C, and distal portion 102B, for example, terminating distally at one or more distal openings (i.e., in a distal most end of endoscope 102). As shown in FIG. 1, when medical device 104, including patch 106, is coupled to endoscope 102 (i.e., during the delivery and positioning), patch 106 and a distal portion of medical device 104 may be coupled to distal portion 102B of endoscope, for example, coupled to and/or extending distally beyond the distal opening(s) of internal lumen(s) 112.

Figure 2A:
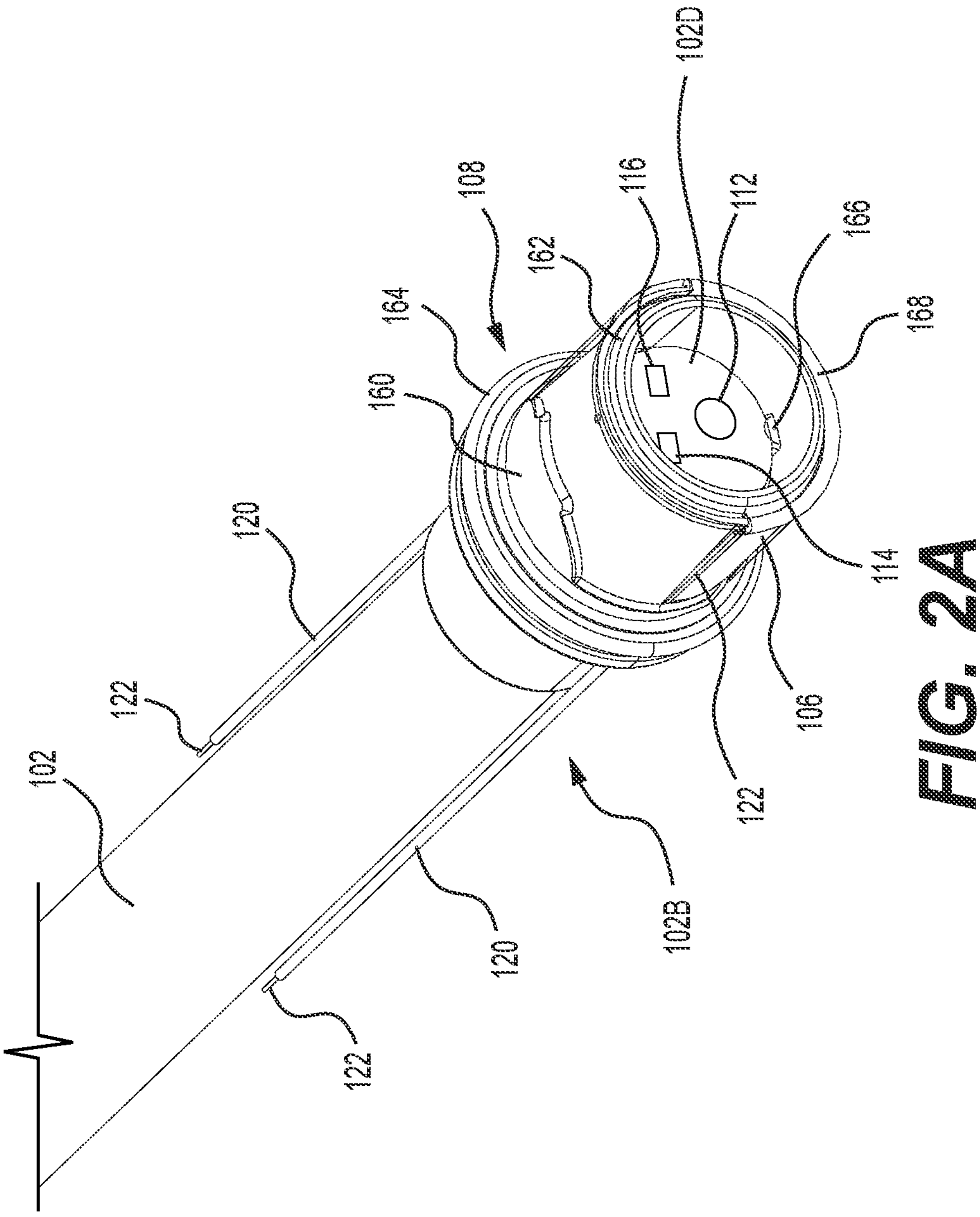
FIGS. 2A and 2B depict perspective views of a distal end of the exemplary medical device of FIG. 1, with FIG. 2A depicting the distal end of the exemplary medical device coupled to a distal end of an endoscope.

Endoscope 102 (i.e., distal portion 102B of endoscope 102) may include a diameter of approximately 9 mm to approximately 15 mm, for example, approximately 10.5 mm to approximately 12 mm. End cap 108 may include a size and/or shape configured to be coupled to (e.g., radially surround) distal portion 102B of endoscope 102. As mentioned, endoscope 102 may include one or more internal lumens 112, for example, a working channel with a diameter of approximately 2 mm to approximately 4 mm, for example, approximately 2.8 mm. Additionally, as shown in FIG. 2A, endoscope 102, for example, a distal end face 102D of endoscope 102, may include one or more illumination device(s) 114 (e.g., one or more LEDs, optical fibers, and/or other illuminators) and/or one or more visualization device(s) 116 (e.g., one or more cameras, one or more image sensors, endoscopic viewing elements, optical assemblies including one or more image sensors and one or more lenses, etc.).

Although not shown, endoscope 102 may include one or more grooves, channels, lumens, or other features to movably receive one or more of control element(s) 120, actuation element(s) 122, and/or sheath element(s) 124. Furthermore, although not shown, one or more portions of endoscope 102 (i.e., distal portion 102B) may be deflectable, for example, via one or more knobs or other controls on a proximal handle. In these aspects, distal portion 102B of endoscope 102 may be maneuvered while being delivered to the treatment site and/or positioned relative to the treatment site, for example, in a retroflex position, which may be used when the treatment site is in the subject's esophagus, stomach, duodenum, colon, or other portion of the GI tract.

Although the treatment site is discussed as being in the subject's GI tract, this disclosure is not so limited, as the treatment site may be any internal lumen or other tissue within the subject. Additionally, although endoscopes are referenced herein, it will be appreciated that the disclosure encompasses any medical devices having a working channel extending from a proximal end to a distal end, such as ureteroscopes, duodenoscopes, gastroscopes, endoscopic ultrasonography ("EUS") scopes, colonoscopes, bronchoscopes, laparoscopes, arthroscopes, cystoscopes, aspiration scopes, sheaths, or catheters.

As shown in FIG. 1, medical device 104 includes end cap 108 and handle 110. One or more control elements 120 and one or more actuation elements 122 may extend from one or more portions of handle 110 to one or more portions of end cap 108. Control element(s) 120 may each be formed by a coil, a tube, a sheath, etc. Actuation element(s) 122 may each be formed by a wire, a coil, a rod, etc. Additionally, one or more sheath elements 124 may also extend from one or more portions of handle 110 to one or more portions of end cap 108. Sheath element(s) 124 may each be formed by a coil, a tube, a sheath, etc. In these aspects, each control element 120 may be radially within a respective sheath element 124. Moreover, each actuation element 122 may be radially within a respective control element 120.

As mentioned above and as discussed in detail below, patch 106 may be movably coupled to end cap 108. For example, movement of one or more control elements 120 may extend, retract, or otherwise position patch 106 relative to end cap 108. Moreover, in some aspects, movement of one or more actuation elements 122 may help to release or deploy patch 106 from end cap 108, for example, to deliver patch 106 to the treatment site, which may help perform hemostasis.

Handle 110 includes a first or stationary body 126 and a second or movable body 128. Movement of movable body 128 relative to stationary body 126 may control the movement (i.e., extension or retraction) of one or more control elements 120, and thus may control the movement (i.e., extension or retraction) of patch 106. In some aspects, handle 110 may include one or more biasing elements (not shown), for example, such that distal movement of movable body 128 relative to stationary body 126 is biased proximally. In these aspects, when the user releases the distal pressure on movable body 128, the one or more biasing elements may move movable body 128 proximally, for example, to the position shown in FIG. 1.

Additionally, handle 110 may include an actuation member 130 that may be movable relative to a portion of movable body 128. For example, actuation member 130 may be movable within a slot 132 within movable body 128. Slot 132 may extend longitudinally in a portion of movable body 128. Movement of actuation member 130 relative to movable body 128 may control the movement of actuation element(s) 122 relative to control element(s) 120, for example, to help release or deploy patch 106. In some aspects, handle 110 may include one or more biasing elements (not shown), for example, such that distal movement of actuation member 130 relative to movable body 128 is biased proximally. In these aspects, when the user releases the distal pressure on actuation member 130, the one or more biasing elements may move actuation member 130 proximally, for example, to the position shown in FIG. 1.

Stationary body 126 may include a handle body 134. Handle body 134 may include a distal portion 134A, a proximal portion 134B, and an intermediate portion 134C. Proximal portion 134B may include a first finger ring 136, for example, to receive a user's thumb. Distal portion 134A may include an end cover 138, for example, at a distal end of handle body 134. End cover 138 may at least partially surround sheath element(s) 124 and may help couple medical device 104 to a portion of endoscope 102 (e.g., to an insertion port). In this aspect, sheath element(s) 124 may be fixedly coupled to stationary body 126 of handle body 134, for example, to distal portion 134A.

Intermediate portion 134C may be generally cylindrical, and may include a handle slot 140. Handle slot 140 may extend longitudinally through at least a portion of intermediate portion 134C of handle body 134. As discussed below, movable body 128 may be coupled to stationary body 126 such that movable body 128 is movable (i.e., longitudinally) over at least a portion of intermediate portion 134C. For example, movable body 128 may surround a portion of intermediate portion 134C, and a portion of movable body 128 may at least partially extend into handle slot 140. Moreover, at least a portion of movable body 128 may be connected to control elements 120.

Movable body 128 may include one or more second finger rings 142, for example, two second finger rings 142. Second finger rings 142 may be coupled to receive two of the user's fingers, such that movement of the fingers (i.e., relative to the user's thumb in first finger ring 136) controls the position of movable body 128 relative to stationary body 126, and thus the movement of control element(s) 120 and/or patch 106. Although two second finger rings 142 are shown, this disclosure is not so limited, and, in some examples, movable body 128 may include a single second finger ring 142.

Figure 4B:
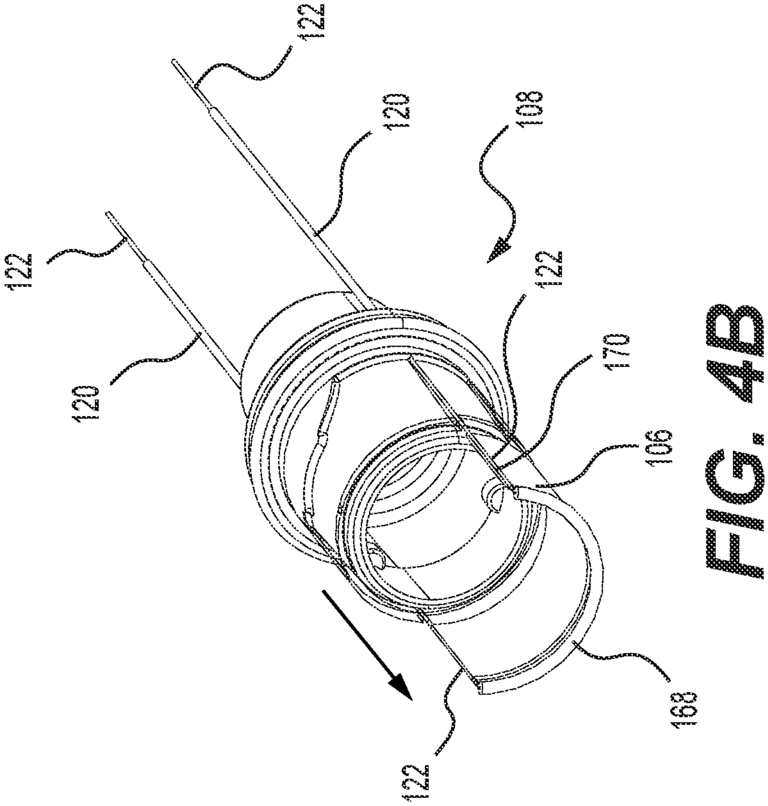
FIG. 4B illustrates a corresponding movement of the distal portion of the exemplary medical device of FIG. 1.
Figure 4A:
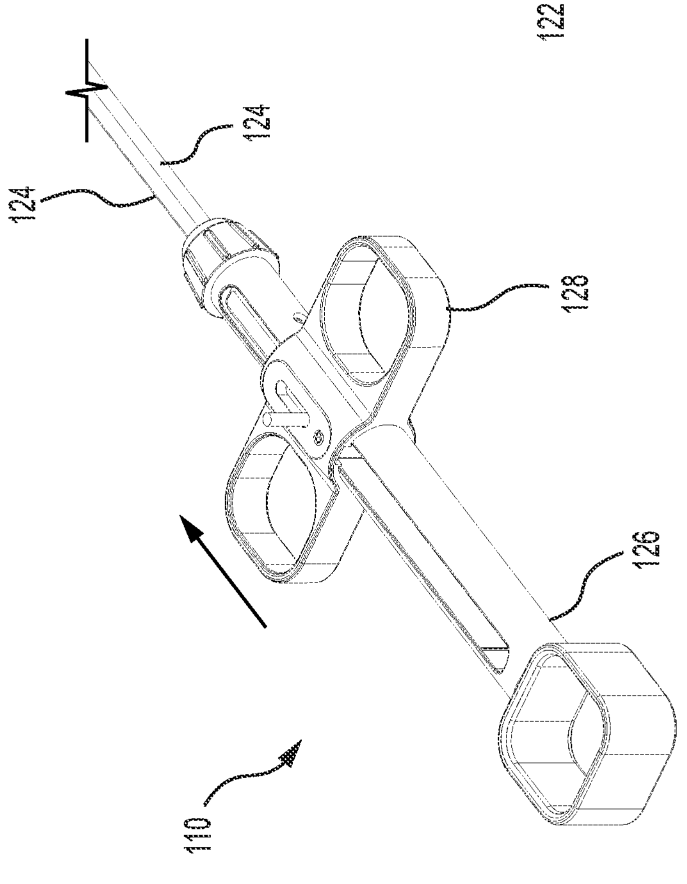
FIG. 4A illustrates actuation of a handle portion of the exemplary medical device of FIG. 1.

In some aspects, stationary body 126 (e.g., a portion of intermediate portion 134C of handle body 134) may include one or more holes 150, for example, circular hole(s), formed in a side of stationary body 126. Additionally, in some aspects, movable body 128 may include one or more extensions or pegs 152. In these aspects, the one or more pegs 152 may at least partially align with the one or more holes 150, for example, when movable body 128 is positioned at one or more locations on stationary body 126. For example, stationary body 126 may include two holes 150 arranged on approximately opposing sides of stationary body 126, and movable body 128 may include two pegs 152 arranged on approximately opposing sides of movable body 128 (e.g., adjacent to second finger rings 142). The one or more pegs 152 may be cantilevered and/or biased to enter the one or more holes 150 when aligned with one or more holes 150. For example, positioning one or more pegs 152 in one or more holes 150 may help to secure the positioning of movable body 128 relative to stationary body 126. Securing the positioning of movable body 128 relative to stationary body 126 may help to secure patch 106 in an extended position, for example, relative to end cap 108. For example, as the user advances movable body 128 distally, peg(s) 152 may at least partially engage with hole(s) 150 as movement of control element(s) 120 extend patch 106 from end cap 108 (FIGS. 4A and 4B). Once patch 106 is extended from end cap 108 a predetermined distance, for example, via movement of movable body 128, the engagement between hole(s) 150 and peg(s) 152 may help to prevent movable body 128 from moving proximally relative to stationary body 126 (e.g., via one or more biasing elements).

Figure 2B:
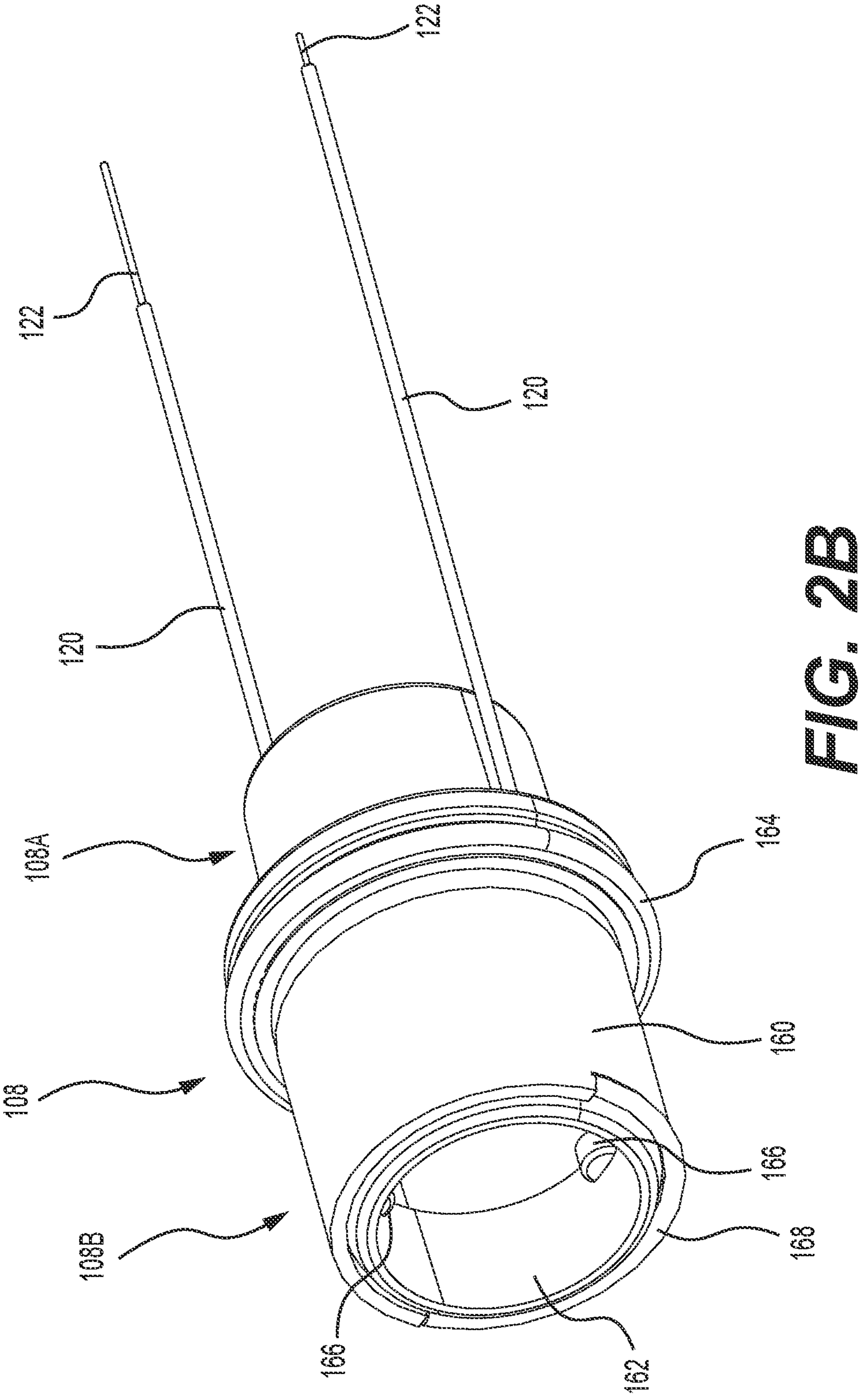

FIGS. 2A and 2B illustrate various features of distal portion 102B of endoscope 102 and end cap 108. FIG. 2A illustrates end cap 108 coupled to endoscope 102, and FIG. 2B illustrates end cap 108 separate from endoscope 102. As mentioned above, distal portion 102B, for example, distal end face 102D, may include one or more of a distal end of a lumen 112, one or more illumination device(s) 114, and one or more visualization device(s) 116.

End cap 108 may be coupled to distal portion 102B, for example, via a friction fit, an adhesive, a press fit, a crimping, or any other appropriate coupling mechanism. Additionally, end cap 108 may receive portions of one or more of control element(s) 120 and actuation element(s) 122. For example, end cap 108 may include an outer cap 160 and an inner cap 162, and patch 106 may be movably positioned between outer cap 160 and inner cap 162. It is noted that FIG. 2A includes a portion of outer cap 160 removed, in order to illustrate a portion of patch 106 between outer cap 160 and inner cap 162. Furthermore, it is noted that one or more portions, or an entirety, of end cap 108 may be transparent, which may help the user to visualize the treatment site and/or patch 106, for example, with visualization device(s) 116 on endoscope 102.

Additionally, end cap 108 may include an end cap ring 164. For example, end cap ring 164 may extend radially outward from end cap 108, for example, between a proximal portion 108A of end cap 108 and a distal portion 108B of end cap 108 (FIG. 2B). Additionally, one or more portions of end cap ring 164 may include a radiopaque material (e.g., one or more markers, one or more gradients, etc.), or otherwise help the user to visualize end cap ring 164 or other portions of end cap 108. In some aspects, sheath element(s) 124 may be coupled (e.g., fixedly coupled) to end cap 108, for example, to end cap ring 164 (e.g., via a friction fit, an adhesive, a press fit, a crimping, or any other appropriate coupling mechanism. Although not shown, end cap ring 164 may include one or more lumens, for example, to movably receive one or more of control element(s) 120 and actuation element(s) 122.

In some aspects, end cap 108 may include one or more prongs 166. One or more prongs 166 may extend radially inward from a portion of end cap 108, for example, radially inward from a portion of inner cap 162. For example, prong(s) 166 may extend radially inward from inner cap 162 at one or more positions proximal of a distal end of inner cap 162. In these aspects, prong(s) 166 may abut a portion of distal end face 102D of endoscope 102. In this aspect, prong(s) 166 may help to ensure appropriate positioning of end cap 108 on distal portion 102B of endoscope 102, for example, by limiting the proximal movement of end cap 108 relative to distal end face 102D of endoscope 102.

Furthermore, end cap 108 may include a protective element 168, for example, a gasket, a buffer, a seal, etc. Protective element 168 may be positioned distal to patch 106. Protective element 168 may help to at least partially cover, seal, or otherwise block a distal opening between outer cap 160 and inner cap 162. In this aspect, protective element 168 may help to protect patch 106 (e.g., from bodily fluids, impacts, scratches, etc.) during delivery and/or positioning of medical system 100 (e.g., distal portion 102B of endoscope 102 and end cap 108) to the treatment site. Protective element 168 may be at least partially circular or cylindrical, and may span a portion of a circumference at a distal end of patch 106. For example, protective element 168 may span approximately 180 degrees of a distal end of end cap 108. Similarly, when patch 106 is coupled to (e.g., positioned within) end cap 108, patch 106 may span a portion of a circumference of inner cap 162, for example, approximately 180 degrees of the circumference of inner cap 162.

Although the figures illustrate two control elements 120, this disclosure is not so limited. For example, in some aspects, medical device 104 may include two or more patches 106, for example, movably coupled to end cap 108. In these aspects, medical device 104 may include two control elements 120 for each patch 106 (e.g., four control elements 120 for two patches 106, etc.), and a corresponding number of actuation element(s) 122 and sheath element(s) 124.

Patch 106 may be a biodegradable and/or biocompatible patch of any suitable shape and any suitable dimension, e.g. based on the nature of the target tissue site. Patch 106 may be flexible and may have any shape such as, e.g., approximately square, approximately rectangular, rounded square, rounded rectangle, ovate, circular, among other possible shapes. In some examples, the thickness of the patch may be on the order of millimeters, e.g. ranging from approximately 0.1 mm to approximately 5.0 mm or, more specifically, from approximately 0.7 mm to approximately 2.0 mm. Patch 106 may be sufficiently sized to cover the target tissue with a margin for resection. Thus, patch 106 can come in many sizes to accomplish such a task. In some aspects, patch 106 may be approximately 50 mm by 50 mm (i.e., approximately 2 inches by 2 inches).

Patch 106 may be of any suitable color, including clear. Patch 106 may be formed of any suitable material, e.g., nettings, meshes, cloths, gelatins, or polysaccharides (chitosan, cellulose, starch, alginates, etc.) that may be further modified with synthetic biocompatible materials (pHEMA, PGA, PLA, PCA, PEG, etc.). In some aspects, patch 106 may be formed of a bioadhesive material, for example, such as chitosan, modified chitosan, cellulose, pHEMA, PVA, PEG, or composites of one or more of these polymers. Additionally, for example, patch 106 may be comprised of polypropylene, polyester, Polytetrafluoroethylene (PTFE), expanded Polytetrafluoroethylene (ePTFE), and/or silicone. Patch 106 may be adhered to the target tissue using materials commonly known in the art, such as, for example, fibrin glue, hydrogel, and/or cyanoacrylate. Alternatively or additionally, patch 106 may be comprised of and/or dosed with agents to prevent the shedding of cells from the target tissue or to treat the target site. In some aspects, patch 106 may include a treatment agent, for example, an antibiotic and/or hemostatic agent. Moreover, after patch 106 is delivered to the treatment site, the user may spray, apply, or otherwise deliver one or more hemostatic agents (e.g., one or more hemostatic powders), for example, through a working channel (e.g., internal lumen 112) of endoscope 102 or another medical device.

Figure 3B:
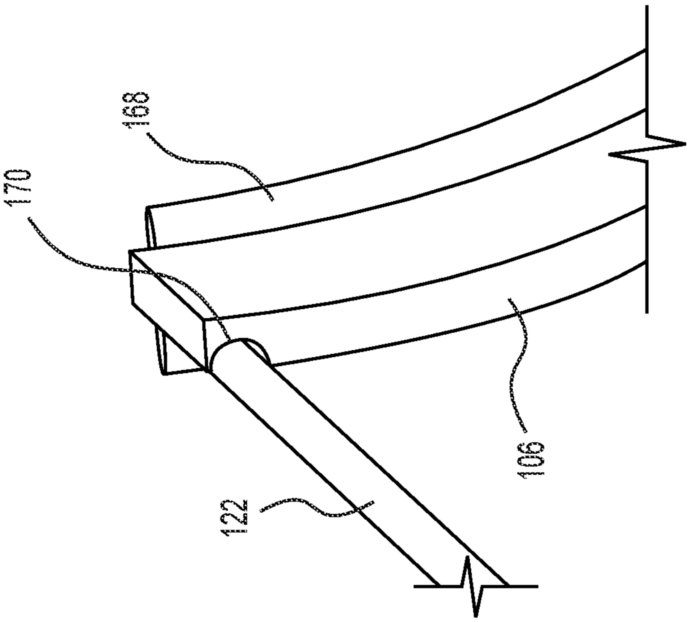
FIGS. 3A and 3B depict perspective views of portions of the distal end of the exemplary medical device of FIG. 1.
Figure 3A:
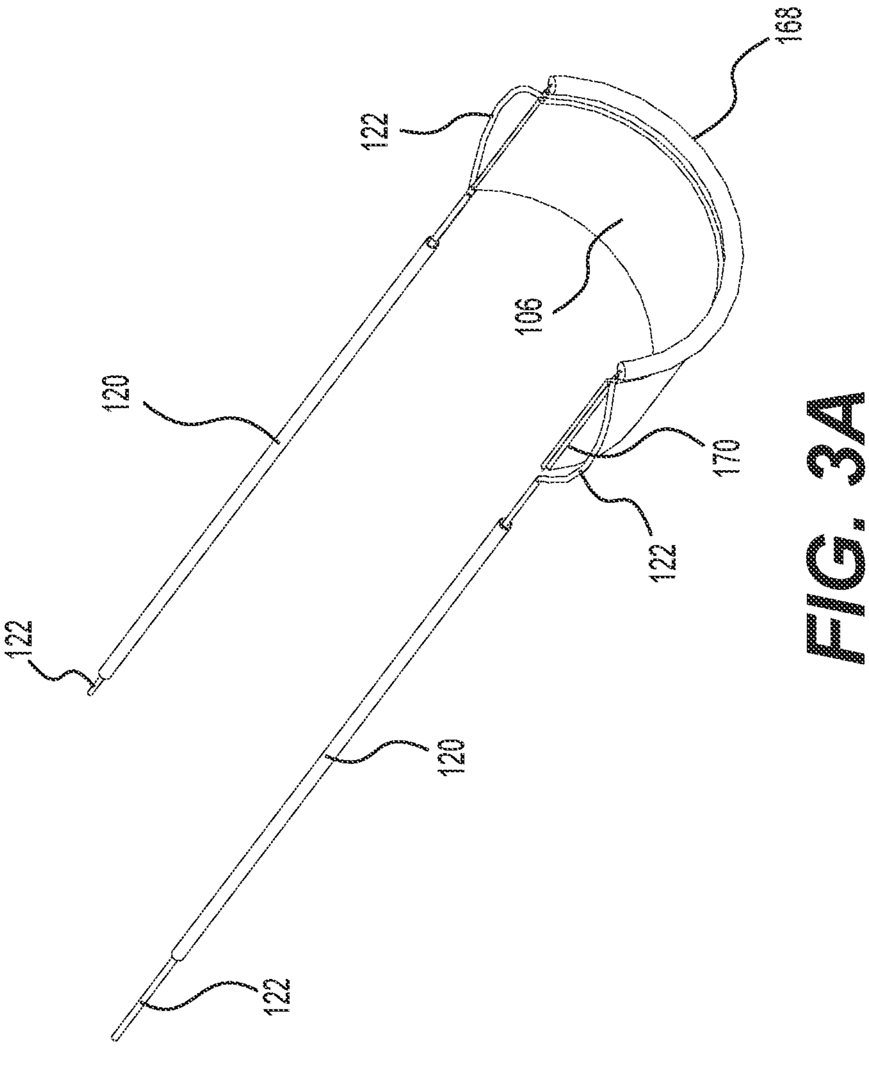

FIGS. 3A and 3B illustrate additional aspects of medical device 104 separate from endoscope 102. For example, FIGS. 3A and 3B illustrate patch 106 and distal portions of control elements 120 and actuation elements 122. It is noted that sheath elements 124 are omitted for clarity. As mentioned above, protective element 168 may be positioned distal to patch 106.

Additionally, patch 106 may include one or more retention grooves 170. As shown in FIGS. 3A and 3B, grooves 170 may be formed by reduced thicknesses of patch 106, for example, a semi-circular indentation on one side of patch 106. Patch 106 may include the one or more retention grooves positioned on a radially exterior portion of patch 106 when patch 106 is in an undeployed configuration. In some examples, patch 106 may include two grooves 170 on opposing sides of patch 106, for example, extending longitudinally through lateral end portions of patch 106. Grooves 170 may extend longitudinally through an entire longitudinal length of patch 106. As discussed in detail below, grooves 170 may receive portions of actuation elements 122. For example, as shown in FIG. 3B, when actuation element(s) 122 are in a straight (e.g., unactuated) configuration, actuation element(s) 122 may be at least partially positioned within groove(s) 170.

In these aspects, actuation element(s) 122 may help to retain patch 106, for example, when patch 106 is extended distally from end cap 108 (FIG. 4B). For example, actuation element(s) 122 may help to retain patch 106 in the curved configuration (FIG. 3A), and may also help to maintain control or a connection to patch 106, for example, in order to position and/or reposition patch 106 (e.g., based on the movement of control elements 120). However, when actuation element(s) 122 are actuated (i.e., advanced distally relative to control element(s) 120), actuation elements(s) 122 may extend, bow, or bend radially outward, as shown in FIG. 3A. For example, actuation element(s) 122 may be formed of a shape-memory material (e.g., Nitinol) or a braided wire, such that when actuation elements 122 are extended distally, actuation elements 122 may take the radially outward extended, bowed, or bent configuration. When actuation element(s) 122 extend, bow, or bend radially outward, portions of actuation element(s) 122 may no longer be positioned within one or more groove(s) 170. As such, actuation of actuation element(s) 122 may release or deploy patch 106, for example, for patch 106 to be applied to tissue at the treatment site.

FIGS. 4A and 4B illustrate portions of medical system 100 and corresponding movements to extend or retract patch 106 from end cap 108. As discussed above and as shown in FIG. 4A, the user may advance movable body 128 distally relative to stationary body 126 of handle 110. Movement (e.g., distal movement) of movable body 128 may distally advance control element(s) 120, for example, within respective sheath element(s) 124. As discussed above and as shown in FIG. 4B, distal movement of control element(s) 120 may distally extend patch 106, for example, relative to end cap 108. Actuation element(s) 122 may be positioned within groove(s) 170 in patch 106, for example, helping to retain patch 106 during the extension. Moreover, protective element 168 may also move distally along with patch 106, for example, helping to prevent patch 106 from inadvertently contacting tissue or other materials at the treatment site. The user may use one or more visualization devices 116 (FIG. 2A) to position patch 106 relative to the treatment site. Additionally, the user may further distally advance and/or proximally retract movable body 128 relative to stationary body 126 to control the position of patch 106 relative to end cap 108.

Figure 5A:
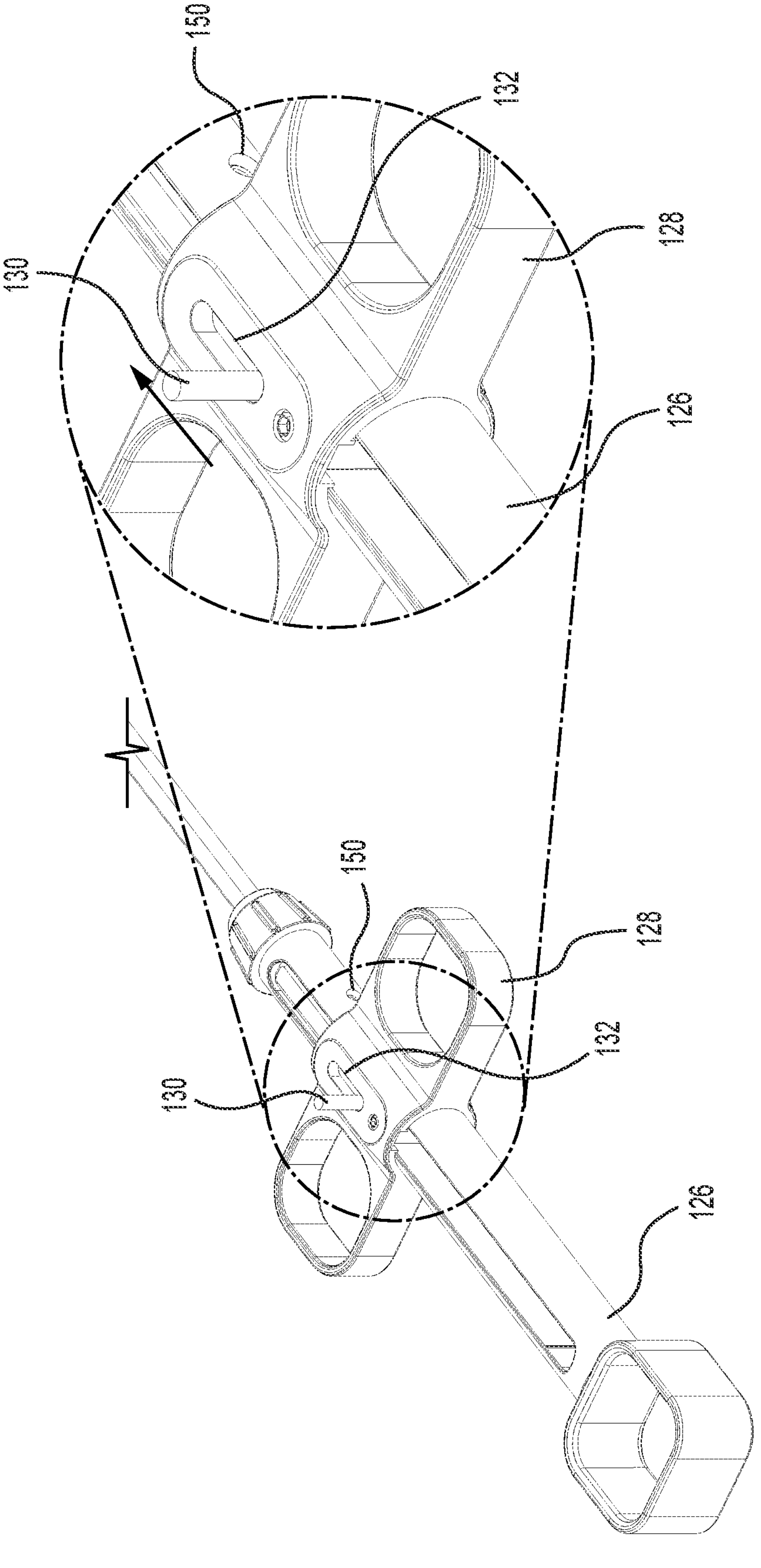
FIG. 5A illustrates additional actuation of the handle portion of the exemplary medical device of FIG. 1.
Figure 5B:
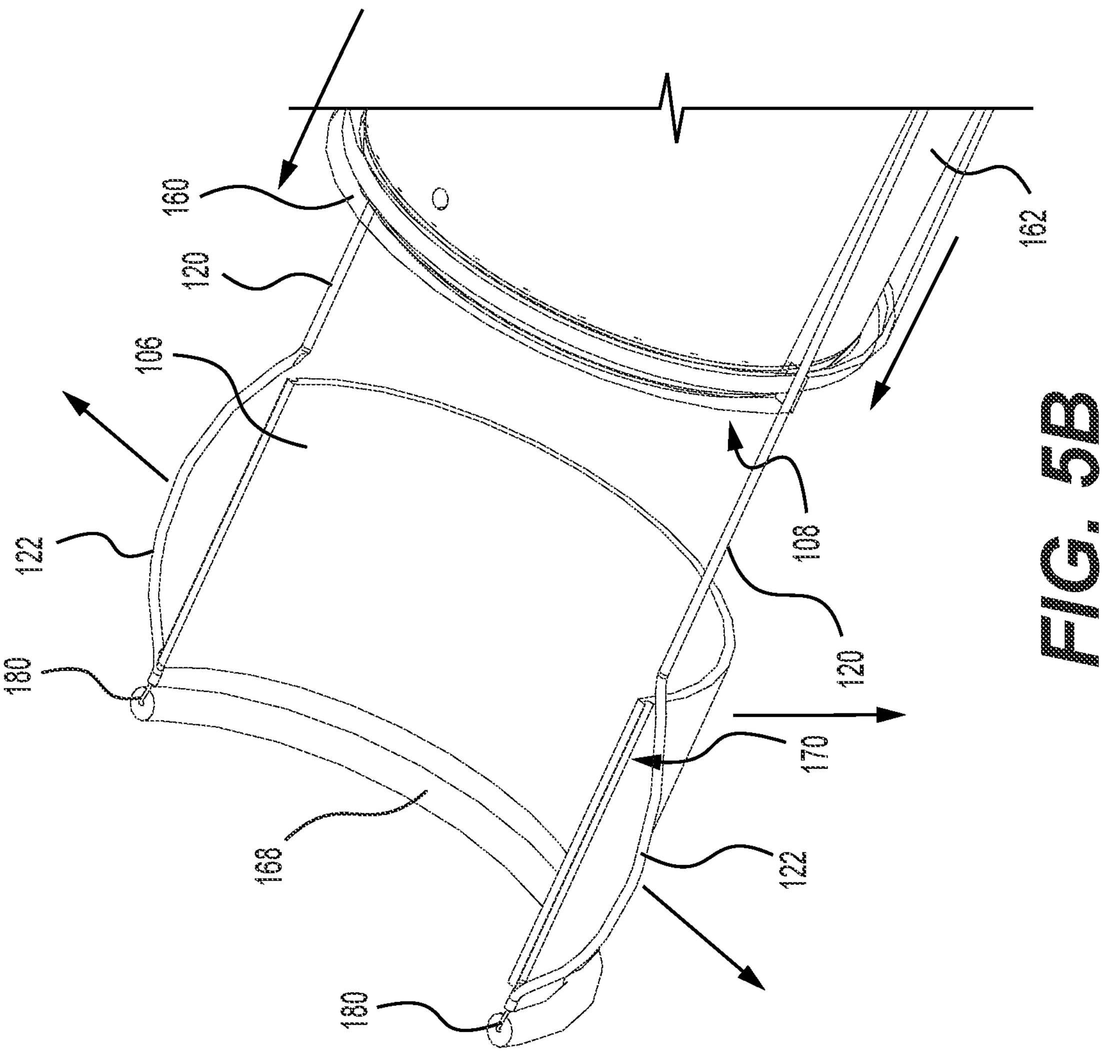
FIG. 5B illustrates a corresponding movement of the distal portion of the exemplary medical device of FIG. 1.

FIGS. 5A and 5B illustrate portions of medical system 100 and corresponding movements to release or deploy patch 106 from end cap 108. As discussed above and as shown in FIG. 5A, with patch 106 in the desired position relative to end cap 108 (and thus with movable body 128 in the desired position relative to stationary body 126) the user may advance actuation member 130 distally, for example, within slot 132.

In some aspects, movable body 128 may be positioned relative to stationary body 126 such that peg 152 (FIG. 1) may be positioned within or otherwise interact with hole 150, for example, securing the position of movable body 128 relative to stationary body 126. As discussed above and as shown in FIG. 5B, advancing actuation member 130 distally within slot 132 may extend actuation element(s) 122, for example, relative to control element(s) 120. For example, with patch 106 extended from end cap 108 (e.g., extending distally of outer cap 160 and inner cap 162), advancing actuation element(s) 122 may cause a distal portion of actuation element(s) 122 to extend, bow, or bend radially outward and out of groove(s) 170, thus releasing patch 106. As mentioned, actuation element(s) 122 may be formed of a shape-memory material (e.g., Nitinol) or a braided wire, such that when actuation elements 122 are extended distally, actuation elements 122 may take the radially outward extended, bowed, or bent configuration. Patch 106 may then be applied to the treatment site. In some aspects, one or more auxiliary medical devices (e.g., a grasper, forceps, etc.) may be delivered to the treatment site (e.g., through internal lumen 112 of endoscope 102) to help position patch 106 at the treatment site. Moreover, as shown in FIG. 5B, actuation element(s) 122 may be connected to protective element 168 at one or more connection points 180. In these aspects, protective element 168 may remain coupled to actuation element(s) 122, even when actuation element(s) 122 take the radially outward extended, bowed, or bent configuration.

Once patch 106 is deployed and delivered to the treatment site, the user may retract actuation element(s) 122 and control elements 120, for example, such that protective element 168 abuts end cap 108 (e.g., outer cap 160 and inner cap 162). Furthermore, the user may inspect patch 106 and the treatment site, for example, using visualization device(s) 116 (FIG. 2A). The user may reposition patch 106, for example, using one or more auxiliary medical devices, as discussed above. Moreover, the user may apply a hemostatic agent (e.g., a hemostatic powder) to the delivered patch 106, for example, via one or more auxiliary medical devices delivered through internal lumen 112.

Various aspects of medical system 100, for example, medical device 104 with patch 106, end cap 108, and handle 110, may have a low cost and may be disposable (i.e., a single use device). Medical device 104 may be coupled to any type of scope to help deliver one or more patches 106 to a treatment site (e.g., endoscopically), and coupling end cap 108 to the distal end of a scope may be quick and user-friendly. The one or more patches 106 may be positioned within end cap 108 (e.g., between outer cap 160 and inner cap 162) and at least partially protected by protective element 168, which may help to protect the one or more patches 106 from fluids, tissues, materials, etc. during the delivery of endoscope 102 to the treatment site.

Additionally, medical device 104 may allow for one or more patches 106 to be delivered to the treatment site in a minimally invasive procedure (e.g., endoscopically), without having to deliver the one or more patches 106 through a working channel (e.g., internal lumen 112) of endoscope 102. In this aspect, the one or more patches 106 may be larger than patches passed through the working channel. Moreover, the one or more patches 106 may not interfere with the delivery of one or more auxiliary medical device, delivery of fluid, application of suction, etc., which may be done through the working channel.

Furthermore, in some aspects, patch 106 may be positioned and repositioned before being deployed. For example, as discussed, the user may manipulate movable body 128 relative to stationary body 126 to position and reposition patch 106 via movement of control element(s) 120. This positioning and repositioning may be done under direct visualization, for example, via visualization device(s) 116. As patch 106 is coupled to endoscope 102 via end cap 108, distal end face 102D of endoscope 102 may be substantially unobstructed. Additionally, in some aspects, the user may lock or otherwise secure the position of movable body 128 relative to stationary body 126, for example, via the interaction of hole 150 and peg 152, or through other handle locking mechanisms.

Once patch 106 is in the desired position, the user may release or deploy patch 106, for example, via movement (e.g., distal movement) of actuation member 130 to control the movement of actuation element(s) 122. As discussed, movement (e.g., distal movement) of actuation element(s) 122 may cause actuation element(s) 122 to extend, bow, or bend radially outward and out of groove(s) 170, thus releasing patch 106. Moreover, patch 106 may be positioned relative to the treatment site using one or more auxiliary medical devices, and/or the user may inspect the position of patch 106 at the treatment site, for example, via visualization device(s) 116. The positioning and deployment of patch 106 (e.g., via movable body 128 and actuation member 130 of handle 110) may be straightforward and user-friendly, which may allow the user to be a surgical technician, while the physician performs one or more other tasks during the procedure.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device, comprising:

a handle, wherein the handle includes a movable body and a stationary body, and wherein the movable body includes an actuation member;

an end cap configured to be coupled to a distal end of a scope;

a patch, wherein the patch is movable relative to the end cap, wherein the patch is coupled to the movable body via one or more control elements such that movement of the movable body extends the patch from the end cap, and wherein the patch is further coupled to the actuation member via one or more actuation elements such that movement of the actuation member bows or bends the one or more actuation elements to at least partially deploy the patch.

2. The medical device of claim 1, wherein the actuation member is movably positioned within a slot on the movable body of the handle.

3. The medical device of claim 1, wherein the end cap includes an outer cap and an inner cap, wherein the patch is movably positioned between the outer cap and the inner cap.

4. The medical device of claim 3, wherein the inner cap includes a prong extending radially inward and configured to abut a distal end face of the scope.

5. The medical device of claim 3, further comprising a protective element positioned at a distal end of the one or more actuation elements and configured to at least partially seal an opening between the outer cap and the inner cap.

6. The medical device of claim 1, wherein the patch includes one or more retention grooves configured to receive a portion of the one or more actuation elements to couple the patch to the one or more actuation elements.

7. The medical device of claim 6, wherein the one or more retention grooves are positioned on a radially exterior portion of the patch when the patch is in an undeployed configuration.

8. The medical device of claim 1, wherein the end cap includes an end cap ring, and wherein at least a portion of the end cap is transparent.

9. The medical device of claim 1, wherein the one or more actuation elements are formed of a shape-memory material.

10. The medical device of claim 1, further comprising one or more sheath elements coupling the handle to the end cap, wherein each of the one or more actuation elements are movably positioned within one of the one or more control elements, and wherein each of the one or more control elements are movably positioned within one of the one or more sheath elements.

11. The medical device of claim 10, wherein the one or more actuation elements are each formed of one or more wires, and wherein the one or more control elements are each formed of one or more coils.

12. The medical device of claim 1, wherein the movable body of the handle is movable within a slot in the stationary body of the handle.

13. The medical device of claim 12, wherein the movable body of the handle includes at least one peg, wherein the stationary body of the handle includes at least one hole, and wherein the at least one peg is configured to engage with the at least one hole to at least partially secure a position of the movable body on the stationary body.

14. The medical device of claim 13, wherein a position of the at least one hole on the stationary body corresponds to a position of the movable body on the stationary body in which the patch is extended from the end cap.

15. The medical device of claim 3, wherein the patch includes a hemostatic agent, and wherein the patch includes a flexible body that spans a circular portion of the inner cap of the end cap.

16. A medical system, comprising:

an endoscope, including a distal end including one or more visualization devices on a distal end face;

a medical device, wherein the medical device includes:

a handle, wherein the handle includes a movable body and a stationary body, and wherein the movable body includes an actuation member;

an end cap configured to be coupled to a radial exterior of the distal end of the endoscope; and a patch, wherein the patch is movable relative to the end cap, wherein the patch is coupled to the movable body via one or more control elements such that movement of the movable body extends the patch from the end cap, and wherein the patch is further coupled to the actuation member via one or more actuation elements such that movement of the actuation member at least partially deploys the patch.

17. The medical system of claim 16, wherein the end cap includes an outer cap and an inner cap, wherein the patch is movably positioned between the outer cap and the inner cap, and wherein the inner cap includes a prong extending radially inward and configured to abut the distal end face of the endoscope.

18. The medical system of claim 17, further comprising a protective element positioned at a distal end of the one or more actuation elements and configured to at least partially seal an opening between the outer cap and the inner cap, and wherein the patch includes one or more retention grooves configured to receive a portion of the one or more actuation elements to couple the patch to the one or more actuation elements, and wherein movement of the one or more actuation elements extends, bows, or bends the one or more actuation elements radially outward and out of the one or more retention grooves.

19. A medical device, comprising:

a handle, wherein the handle includes a movable body and a stationary body, and wherein the movable body includes an actuation member that is movable within a slot in the movable body;

an end cap configured to be coupled to a distal end of a second medical device, wherein the end cap includes an outer cap and an inner cap;

a patch, wherein the patch is movably positioned between the outer cap and the inner cap; and a protective element configured to at least partially seal a distal opening between the outer cap and the inner cap;

wherein the patch is coupled to the movable body via one or more control elements such that distal movement of the movable body extends the patch from the end cap, and wherein the patch is further coupled to the actuation member via one or more actuation elements such that movement of the actuation member at least partially deploys the patch, wherein the protective element is coupled to a distal end of each of the one or more actuation elements.

20. The medical device of claim 19, wherein the inner cap includes a prong extending radially inward and configured to abut a distal end face of the second medical device, wherein the patch includes one or more retention grooves configured to receive a portion of the one or more actuation elements to couple the patch to the one or more actuation elements, and wherein movement of the one or more actuation elements causes the one or more actuation elements to, bow or bend radially outward and out of the one or more retention grooves to at least partially deploy the patch.

* * * * *